US009273334B2

(12) United States Patent
Zhou et al.

(10) Patent No.: US 9,273,334 B2
(45) Date of Patent: Mar. 1, 2016

(54) METHODS OF PRODUCING PROTOPORPHYRIN IX AND BACTERIAL MUTANTS THEREFOR

(71) Applicant: The Board of Regents of the University of Oklahoma, Norman, OK (US)

(72) Inventors: Jizhong Zhou, Norman, OK (US); Dongru Qiu, Hubei (CN); Zhili He, Norman, OK (US); Ming Xie, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 14/349,171

(22) PCT Filed: Mar. 14, 2014

(86) PCT No.: PCT/US2014/028689

§ 371 (c)(1),
(2) Date: Apr. 2, 2014

(87) PCT Pub. No.: WO2014/144329

PCT Pub. Date: Sep. 18, 2014

(65) Prior Publication Data

US 2016/0002687 A1 Jan. 7, 2016

Related U.S. Application Data

(60) Provisional application No. 61/788,036, filed on Mar. 15, 2013.

(51) Int. Cl.
*A61K 8/49* (2006.01)
*C12P 17/18* (2006.01)
*C12N 9/88* (2006.01)

(52) U.S. Cl.
CPC ................. *C12P 17/182* (2013.01); *C12N 9/88* (2013.01); *C12Y 499/01001* (2013.01)

(58) Field of Classification Search
CPC .................................................... A61K 8/4953
USPC ............................................. 435/252.3, 69.1
See application file for complete search history.

(56) References Cited

U.S. PATENT DOCUMENTS

| | | | |
|---|---|---|---|
| 5,298,502 | A | 3/1994 | Halling et al. |
| 2005/0089972 | A1 | 4/2005 | Schmidt-Dannert et al. |

OTHER PUBLICATIONS

GENBANK_CP000606, Shewanella Ioihica PV-4, complete genome, Nov. 21, 2011; pp. 1 and 209 included with this IDS. Definition, Organism, and Reference; p. 209, the last gene, 'Shew_ 1140 . . . ferrochelatase'; p. 409, the last gene, 'Shew_2229 . . . ferrochelatase'; Nucleotide sequence between 1314559-1315626 and 2606331-2605318.

Newton et al.; "Analysis of current-generating mechanisms of Shewanella Ioihica PV-4 and Shewanella oneidensis MR-1 in microbial fuel cells." Appl Environ Microbiol. 2009, vol. 75(24), p. 7674-81.

Jain et al.; "Electron transfer mechanism in Shewanella loihica PV-4 biofilms formed at graphite electrode." Bioelectrochemistry. 2012, vol. 87, p. 28-32.

Warner et al.; "Characterization of an NADH-dependent persulfide reductase from Shewanella Ioihica PV-4: implications for the mechanism of sulfur respiration via FAD-dependent enzymes." Biochemistry, 2011, vol. 50(2), p. 194-206.

Yuan et al.; "Functional Assessment of EnvZ/OmpR Two-Component System in Shewanella oneidensis, PLoS One." 2011, col. 6(8):e23701. PDF file: p. 1-9.

NCBI_YP_001094354, Ferrochelatase [Shewanella Ioihica PV-4] Jan. 24, 2012, [online], Oct. 26, 2015.

Nakahigashi et al.; "Photosensitivity of a protoporphyrin-accumulating, ligh-sensitive mutant (visA) of *Escherichia coli* K-12." Proc. Natl. Aca. Sci. USA vol. 88, pp. 10520-10524 Dec. 1991.

Miyamoto et al.; "Acumulation of protoporphyrin IX in light-sensitive mutants of *Escherichia coli*." FEBS 11602, vol. 310(3) pp. 246-248 Oct. 1992.

Notification of Transmittal of the International Search Report & Written Opinion in PCT/US14/28689; dated Sep. 12, 2014; pp. 1-22.

*Primary Examiner* — Maryam Monshipouri
(74) *Attorney, Agent, or Firm* — Dunlap Codding, P.C.

(57) ABSTRACT

The presently disclosed inventive concepts are directed in certain embodiments to a method of producing protoporphyrin IX by (1) cultivating a strain of *Shewanella* bacteria in a culture medium under conditions suitable for growth thereof, and (2) recovering the protoporphyrin IX from the culture medium. The strain of *Shewanella* bacteria comprises at least one mutant hemH gene which is incapable of normal expression, thereby causing an accumulation of protoporphyrin IX. In certain embodiments of the method, the strain of *Shewanella* bacteria is a strain of *S. loihica*, and more specifically may be *S. loihica* PV-4. In certain embodiments, the mutant hemH gene of the strain of *Shewanella* bacteria may be a mutant of shew_2229 and/or of shew_1140. In other embodiments, the presently disclosed inventive concepts are directed to mutant strains of *Shewanella* bacteria having at least one mutant hemH gene which is incapable of normal expression, thereby causing an accumulation of protoporphyrin IX during cultivation of the bacteria. In certain embodiments the strain of *Shewanella* bacteria is a strain of *S. loihica*, and more specifically may be *S. loihica* PV-4. In certain embodiments, the mutant hemH gene of the strain of *Shewanella* bacteria may be a mutant of shew_2229 and/or shew_1140.

11 Claims, 6 Drawing Sheets

METHODS OF PRODUCING PROTOPORPHYRIN IX AND BACTERIAL MUTANTS THEREFOR

CROSS REFERENCE TO RELATED APPLICATIONS/INCORPORATION BY REFERENCE STATEMENT

This application is a 35 USC §371 national stage application of PCT Application No. PCT/US14/29689, filed Mar. 14, 2014; which claims benefit under 35 USC §119(e) of Provisional Application U.S. Ser. No. 61/788,036. The entirety of each of the above-referenced applications are hereby expressly incorporated herein by reference.

STATEMENT REGARDING FEDERALLY SPONSORED RESEARCH OR DEVELOPMENT

This invention was made with government support under Contract Number DE-FG02-07ER64383 awarded by the Department of Energy (DOE). The government has certain rights in the invention.

BACKGROUND

Protoporphyrin IX (7,12-diethenyl 3,8,13,17-tetramethyl-21H,23H-porphine 2,18 dipropanoic acid) is the direct precursor of heme B (Fe-protoporphyrin IX), hemin (heme B with a chloride ligand), and hematin (hemin with a hydroxide ligand in place of the chloride). Heme is the prosthetic group for hemoproteins including hemoglobin and catalases, which are crucial for respiration and detoxification in humans and animals. The photosensitivity of protoporphyrin IX has been utilized in photodynamic therapy (PDT), a therapy against different forms of cancer. Protoporphyrin IX has been used as a therapeutic supplement for patients with infective hepatitis and chronic liver diseases. The biological heme synthesis pathway is very conservative among prokaryotes (e.g. bacteria) and eukaryotes (e.g., human). Ferrochelatase (EC 4.99.1.1) is the terminal enzyme in the heme biosynthesis pathway and catalyzes the insertion of $Fe^{2+}$ into protoporphyrin IX. In the best-studied laboratory model bacterium *Escherichia coli* K12 strain, a hemH mutant is sensitive to visible light due to the accumulation of protoporphyrin IX. This is similar to the defect observed in human protoporphyria (Miyamoto et al. *J Mol Biol.* 1991, 219(3):393-398; Miyamoto et al. *FEBS Lett.* 1992, 310(3):246-248; Miyamoto et al. *J Biochem.* 1994, 115(3):545-551; Nakahigashi et al. *Proc Natl Acad Sci USA.* 1991, 88(23):10520-10524).

The price of protoporphyrin IX is about 36,000 $US/kg in the world market, and the products are usually extracted from livestock blood. It is known that such blood-based production processes are high cost, may cause contamination to the environment (e.g., due to use of large amounts of chemicals), and may present health risks to humans and animals (e.g., due to viruses and prions). The chemical synthesis of protoporphyrin has been proposed, but has not been commercially feasible due to high cost and possible contamination.

DETAILED DESCRIPTION

Figure 1:
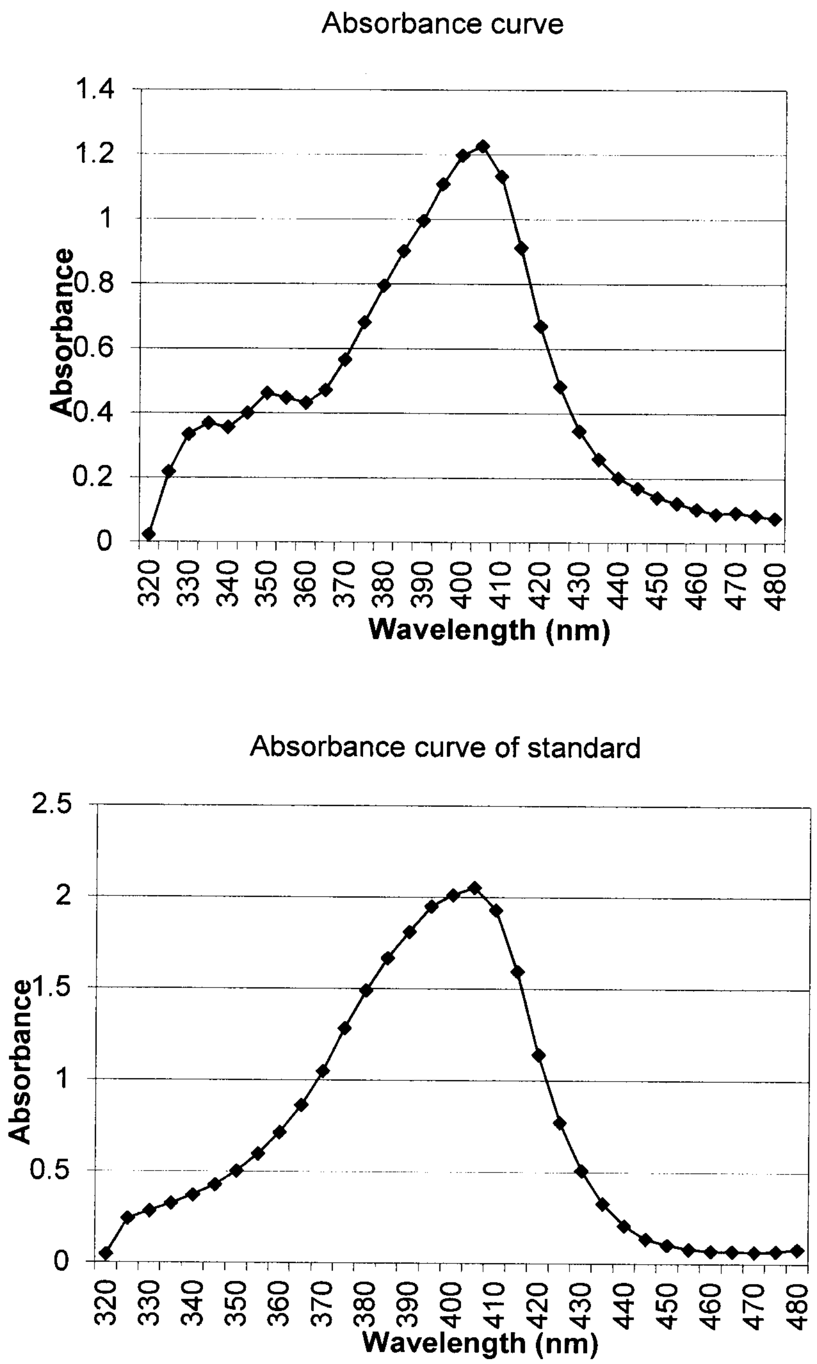
FIG. 1. Ultraviolet-visible spectrograms of the "bacterial product" comprising protoporphyrin IX (PPIX) produced by a *Shewanella loihica* PV-4 mutant of the presently disclosed inventive concepts (upper panel), and a commercially-available PPIX standard (lower panel).

The presently disclosed inventive concepts are directed to using certain bacterial mutants for producing protoporphyrin IX (PPIX) and heme products in a less costly and biologically and environmentally safer way than previously available methods. The methods described herein produce protoporphyrin IX of high quality, high yield, and low cost via relatively simple processes which reduce the possibility of environmental contamination and risk to health.

Before explaining at least one embodiment of the inventive concepts in detail by way of exemplary description, drawings, experimentation, examples, results, and laboratory procedures, it is to be understood that the presently disclosed inventive concepts are not limited in their application to the details of methods, arrangement of steps, compositions, components, and/or construction as set forth in the following description or illustrated in the drawings, experimentation, examples, procedures and/or results. The presently disclosed inventive concepts are capable of other embodiments or of being practiced or carried out in various ways not explicitly described herein. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting except where indicated as such. Moreover, in the following detailed description, numerous specific details are set forth in order to provide a more thorough understanding of the disclosure. However, it will be apparent to a person having ordinary skill in the art that the presently disclosed inventive concepts may be practiced without these specific details. In other instances features which are well-known to persons of ordinary skill in the art have not been described in detail to avoid unnecessary complication of the description.

Unless otherwise defined herein, scientific and technical terms used in connection with the presently disclosed inventive concepts shall have the meanings that are commonly understood by those of ordinary skill in the art. Further, unless otherwise required by context, singular terms shall include pluralities and plural terms shall include the singular.

Generally, nomenclatures utilized in connection with, and techniques of, biotechnology including cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well-known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and biotechnology described herein are those well-known and commonly used in the art. Standard techniques are used for chemical syntheses, chemical analyses, and biotechnological syntheses and preparation.

All patents, published patent applications, and non-patent publications mentioned herein are indicative of the level of skill of those skilled in the art to which the presently disclosed inventive concepts pertain. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed and claimed herein can be made and executed without undue experimentation in light of the present disclosure. While the compositions and methods of the presently disclosed inventive concepts have been described in terms of particular embodiments, it will be apparent to those of skill in the art that variations may be applied to the sequences, mutants, compositions and/or methods and in the steps or in the sequence of steps of the methods described herein without departing from the concept, spirit and scope of the presently disclosed inventive concepts. All such similar substitutes and modifications apparent to those skilled in the art are deemed to be within the spirit, scope and concept of the inventive concepts as defined herein.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" (by way of example) will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

Throughout the specification and claims, unless the context requires otherwise, the terms "substantially" and "about" will be understood to not be limited to the specific terms or amounts qualified by these adjectives/adverbs, but will be understood to indicate a value includes the inherent variation of error for the device or composition, the method being employed to determine the value and/or the variation that exists among study subjects. Thus, said terms allow for minor variations and/or deviations that do not result in a significant impact thereto. For example, in certain instances the term "about" is used to indicate that a value includes the inherent variation of error for the device, the method being employed to determine the value and/or the variation that exists among study subjects. For example but not by way of limitation, when the term "about" is utilized, the designated value may vary by plus or minus fifteen percent, plus or minus twelve percent, or plus or minus eleven percent, or plus or minus ten percent, or plus or minus nine percent, or plus or minus eight percent, or plus or minus seven percent, or plus or minus six percent, or plus or minus five percent, or plus or minus four percent, or plus or minus three percent, or plus or minus two percent, or plus or minus one percent, or plus or minus one-half percent. Similarly, the term "substantially" may also relate to 80% or higher, such as 85% or higher, or 90% or higher, or 95% or higher, or 99% or higher, and the like. For example, the term "substantially" means that the subsequently described event or circumstance occurs at least 80% of the time, or at least 85% of the time, or at least 90% of the time, or at least 95% of the time, or at least 98% of the time. In general, the term "substantially" will be understood to allow for minor variations and/or deviations that do not result in a significant impact thereto.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "protein product" as used herein includes natural, recombinant, and/or synthetic proteins, biologically active protein variants (including variants due to insertions, substitutions and deletions), and chemically modified derivatives thereof. Included are protein products that are substantially homologous to the natural protein products disclosed herein.

The term "biologically active" as used herein means that the protein product demonstrates similar properties, but not necessarily all of the same properties, and not necessarily to the same degree, as the natural protein products described herein. Further, by "biologically active" is meant the ability to modify the physiological system of an organism without reference to how the active agent has its physiological effects.

As used herein, "substantially pure" or "pure" means a particular object species is the predominant species present (i.e., on a molar basis it is more abundant than any other individual species in the composition). A substantially purified fraction is a composition wherein the object species comprises at least about 50 percent (on a molar basis) of all macromolecular species present. Generally, a substantially pure composition will comprise more than about 70 percent of all macromolecular species present in the composition, or more than about 75%, or more than about 80%, or more than about 85%, or more than about 90%, or more than about 95%, or more than about 99%. In certain embodiments, the object species is purified to essential homogeneity (contaminant species cannot be detected in the composition by conventional detection methods) wherein the composition consists essentially of a single macromolecular species. The term "pure" or "substantially pure" also refers to preparations where the object species is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

The term "substantially homologous" as used herein means a nucleic acid (or fragment thereof) or a protein (or a fragment thereof) having a degree of homology to the corresponding reference nucleic acid or protein that may be in excess of 70%, or in excess of 80%, or in excess of 85%, or in excess of 90%, or in excess of 95%, or in excess of 96%, or in excess of 97%, or in excess of 98%, or in excess of 99%. For example, in regard to peptides or polypeptides, the percentage of homology as described herein is typically calculated as the percentage of amino acid residues found in the smaller of the two sequences which align with identical amino acid residues in the sequence being compared, when four gaps in a length of 100 amino acids may be introduced to assist in that alignment (as set forth by Dayhoff, in *Atlas of Protein Sequence and Structure*, Vol. 5, p. 124, National Biochemical Research Foundation, Washington, D.C. (1972)). In one embodiment, the percentage homology as described above is calculated as the percentage of the components found in the smaller of the two sequences that may also be found in the larger of the two sequences (with the introduction of gaps), with a component being defined as a sequence of four, contiguous amino acids. Sequence identity or homology can be determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul, *Proc. Natl. Acad. Sci. USA* 1990, 87, 2264-2268, modified as in Karlin & Altschul, *Proc. Natl. Acad. Sci. USA* 1993, 90, 5873-5877.

Another example of a mathematical algorithm used for comparison of sequences is the algorithm of Myers & Miller, CABIOS 1988, 4, 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, *Proc. Natl. Acad. Sci. USA* 1988, 85, 2444-2448.

Another algorithm is the WU-BLAST (Washington University BLAST) version 2.0 software (WU-BLAST version 2.0 executable programs for several UNIX platforms). This program is based on WU-BLAST version 1.4, which in turn is based on the public domain NCBI-BLAST version 1.4 (Altschul & Gish, 1996, Local alignment statistics, Doolittle ed., *Methods in Enzymology* 266, 460-480; Altschul et al., *Journal of Molecular Biology* 1990, 215, 403-410; Gish & States, Nature Genetics, 1993, 3: 266-272; Karlin & Altschul, 1993, *Proc. Natl. Acad. Sci. USA* 90, 5873-5877; all of which are incorporated by reference herein). In addition to those otherwise mentioned herein, mention is made too of the programs BLAST, gapped BLAST, BLASTN, BLASTP, and PSI-BLAST, provided by the National Center for Biotechnology Information. These programs are widely used in the art for this purpose and can align homologous regions of two amino acid sequences. In all search programs in the suite, the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

The terms "polynucleotide sequence" or "nucleic acid," as used herein, include any polynucleotide sequence which encodes a respective protein product including polynucleotides in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

The terms "infection," "transduction," and "transfection" are used interchangeably herein and mean introduction of a gene, nucleic acid, or polynucleotide sequence into cells such that the encoded protein product is expressed. The polynucleotides of the presently disclosed inventive concepts may comprise additional secondary sequences useful for the expression of the sequence of primary interest, such as additional coding sequences within the same transcription unit, controlling elements such as promoters, ribosome binding sites, transcription terminators, polyadenylation sites, additional transcription units under control of the same or different promoters, sequences that permit cloning, expression, homologous recombination, and transformation of a host cell, and any such construct as may be desirable to provide embodiments of the presently disclosed inventive concepts.

In one embodiment, the presently disclosed inventive concepts comprise a nucleic acid variant having identity or homology of at least 80%, at least 85%, at least 90%, at least 91%, at least 92%, at least 93%, at least 94%, at least 95%, at least 96%, at least 97%, at least 98%, or at least 99% to at least one or more of SEQ ID NO:1 and SEQ ID NO:2. In another embodiment, the presently disclosed inventive concepts comprise a polypeptide variant having identity or homology of at least 80%, at least 85%, at least 90%, at least 91%, at least 92%, at least 93%, at least 94%, at least 95%, at least 96%, at least 97%, at least 98%, or at least 99% to a polypeptide encoded by at least one of SEQ ID NO:1 and SEQ ID NO:2. In some embodiments, the nucleic acid variant is a DNA which hybridizes with a DNA described above under stringent conditions. By "DNA which hybridizes under stringent conditions" is meant DNA obtained by colony hybridization, plaque hybridization or Southern blot hybridization using DNA encoding klotho protein, specifically including DNA identified after hybridization, using a filter on which colony- or plaque-derived DNA has been immobilized in the presence of 0.7 to 1.0 M NaCl at 65° C. and washing the resulting filter using 0.1 to 2×SSC solutions (the composition of 1×SSC solution comprises 150 mM sodium chloride and 15 mM sodium citrate) at 65° C. Hybridization can be carried out according to a method described, for example, in Molecular Cloning, A Laboratory Manual, the 2nd edition (Sambrook, Fritsch, & Maniatis eds., Cold Spring Harbor Laboratory Press, 1989).

Certain embodiments of the presently described inventive concepts include methods of producing PPIX in bacteria at levels far above those previously known from bacterial levels, which reach commercially-viable amounts. A particularly desirable and novel feature of the mutants (including but not limited to mutants of *Shewanella loihica* PV-4) and processes described herein is that these strains with hemH mutations can produce PPIX at significantly higher levels of accumulation than other species. Thus, certain embodiments of the presently disclosed inventive concepts include any *Shewanella loihica* PV-4 mutant or other *Shewanella loihica* strain or other *Shewanella* strain in which the presently described genes (hemH1 as shew_2229 and hemH2 as shew_1140) have been mutated to be able to provide enhanced PPIX accumulation. These mutants may be produced by methods which include but are not limited to: (1) any method that disrupts expression of the DNA of the hemH1 gene, or hemH2 gene, including but not limited to, insertion of a DNA nucleotide or polynucleotide into the gene, deleting part of or the entire open reading frame of the gene, substitution of bases, and gene duplication, etc., (2) any method that manipulates the mRNA of hemH1 gene or hemH2 gene and that results in reduced production of its mRNA, or the quality of the mRNA, (3) any method that manipulates the protein (ferrochelatase) encoded by hemH1 gene or hemH2 gene and that results in reduced production of this protein (such as RNA interference), or negatively affects the quality of this protein, or negatively affects the catalytic efficiency of this protein.

Ferrochelatase encoded by shew_2229 and shew_1140 catalyzes the insertion of ferrous ion into the PPIX ring to form protoheme in *Shewanella loihica* PV-4. The native *Shewanella loihica* PV-4 strain used as the original basis for at least some of the mutants of the presently disclosed inventive concepts was isolated from iron-rich microbial mats at an active, deep sea, hydrothetmal Naha Vent (1325 m below sea level), located on the South Rift of Loihi Seamount, Hi. The genome of this strain was sequenced by the DOE Joint Genome Institute OD and is publicly accessible. Based on this genome information, research on its mechanisms of bioremediation have been conducted herein by the generation of mutants for functional screening and identification of key genes involved in bioremediation. First, the type II modification and restriction system genes (loci shew_0992 and shew_0993, encoding a restriction endonuclease similar to Pst1) were deleted in order to facilitate the gene manipulation in this strain. Transposon mutagenesis was also conducted on the pst1-free PV-4 strain, and a number of mutants were able to be generated. Among those mutants, some notably red colonies were observed and isolated. The transposon insertion was mapped to the hemH1 gene coding for a ferrochelatase, which is responsible for inserting the ferrous ion into protoporphyrin to make heme. It was predicted that protoporphyrin IX was synthesized and accumulated, conferring a red colony phenotype, since no functional heme-containing proteins could be formed in this hemH1-disrupted mutant. In-frame deletion mutants of hemH1 and hemH2 were also generated. The production levels of protoporphyrin IX and heme were also measured by using spectrofluorometry with the Sigma reagent (P8293) as the standard. In certain embodiments, the production levels of PPIX reached and exceeded around 0.1 mg/ml of culture broth at 30° C. and 250 rpm of shaking for 24 hours.

Because of the insolubility of PP IX, it aggregated and formed a pigment layer on the top of cell pellets after centrifugation. This pigment layer could be separated, extracted, and purified by simple physical methods, thus enabling enhanced purification when scaled up in commercial production processes.

As noted above, particular embodiments of the presently disclosed inventive concepts include methods of using certain bacterial mutants for producing PPIX and/or heme products in a less costly and biologically and environmentally safer way than previously available methods. Suitable bacterial strains have been developed, and bacterial mutants with high yield of PPIX (for example, but not limited to, at least about 0.1 mg/ml in the Luria-Bertani broth) have been generated. Due to the simple preparation methods, the use of few chemical reagents, and the high yield of PPIX production, environmental pollution will be greatly reduced. The presently disclosed inventive concepts are directed, in certain embodiments, to (1) bacterial mutants, including but not limited to, *Shewanella* strains, such as *S. loihica* strains, and particularly *S. loihica* PV-4, which include mutations in at least one of the hemH1 (also referred to herein as Shew_2229) and hemH2 (also referred to herein as Shew_1140) genes, and which are able to overproduce PPIX, and to (2) their use in the production of PPIX and/or heme and/or other heme-based products such as hemin and hematin.

More particularly, certain embodiments of the presently disclosed inventive concepts are directed to any *S. loihica* PV-4 strain which contains a mutation in at least one of the hemH1 and hemH2 genes and which causes overproduction of PPIX. Certain embodiments of the presently disclosed inventive concepts are further directed to any bacterial species or strain, particularly *Shewanella* strains, and more particularly *S. loihica*, which contains a mutation in at least one of the hemH1 and hemH2 genes and which causes overproduction of the PPIX compounds (for example, at a rate of at least 0.1 mg/ml of culture broth). Certain embodiments of the presently disclosed inventive concepts are directed to methods of bacterial production of PPIX and/or heme using the bacterial mutants described above or otherwise contemplated herein. Certain embodiments of the presently disclosed inventive concepts are also directed to methods of bacterial production of PPIX and/or heme using bacterial mutants other than *Shewanella* (including but not limited to *Shewanella oneidensis* MR-1) which comprise mutant versions of hemH1 (shew__2229) and/or hemH2 (shew__1140) genes of strain *S. loihica* PV-4. Further embodiments of the presently disclosed inventive concepts are also directed to methods of bacterial production of PPIX and/or heme using *Shewanella* mutants which comprise mutant versions of hemH1 and/or hemH2 genes from bacteria other than *Shewanella*.

Novel bacterial mutants, of for example *S. loihica* PV-4, in which hemH1 and/or hemH2 have been completely or partially inactivated, can be used in the presently disclosed methods for producing PPIX. The inactivation of the genes can be caused by any effective means by which a gene can be disrupted, including but not limited to insertions, deletions, substitutions, and inversions. Without wishing to be bound by theory, it is thought that the production of PPIX in the mutant bacteria is caused by blockage of the step in which PPIX is converted to heme.

Certain embodiments of the presently disclosed inventive concepts are intended to include any technique, method, and/or means which results in a modification of (1) a shew__2229 and/or shew__1140 DNA sequence (including a related shew__2229 and/or shew__1140 promoter sequence or other expression sequence); (2) the transcription or translation process of shew__2229 and/or shew__1140, and/or (3) the enzyme activity of shew__2229 and/or shew__1140 protein which results in overproduction and accumulation of PPIX. These techniques, methods, and means include, but are not limited to: (1) any method which modifies the DNA sequence of shew__2229 and/or shew__1140 genes e.g., by adding a DNA fragment into any position of the open reading frame (ORF), deleting part of or the entire ORF of the gene, substitution of single bases or multiple bases in the ORF, and/or modification (deletion, insertion, inversion and/or substitution of bases) of the promoter sequences to alter expression of the gene; (2) any method that modifies the mRNA of the shew__2229 and/or shew__1140 genes and that results in reduced production of mRNA and/or the quality, lifespan, and/or the proper function of the mRNA; (3) any method that uses RNA interference (RNAi) by introducing anti-sense RNA into the cell to prevent shew2229 and/or shew__1140 mRNA from properly translated into protein; or (4) any method that modifies the ferrochelatase protein encoded by shew__2229 and/or shew__1140 gene that reduces production of the protein (such as by RNA interference), reduces the quality/lifespan of this protein (such as change of amino acid sequence), and/or reduces the catalytic efficiency of this protein (such as the use of protein inhibitor, or modify protein sequence).

EXAMPLES

Examples of the presently disclosed inventive concepts are provided herein below. However, it is to be understood that the presently disclosed inventive concepts are not to be limited to the specific experimentation, results, and laboratory procedures of the Examples. Rather, the Examples are simply provided as various embodiments of the presently disclosed inventive concepts and are meant to be exemplary, not exhaustive.

Example 1

A series of chemical analyses were conducted to determine the structure of the bacterial products produced by the novel mutants constructed in accordance with the presently disclosed inventive concepts. The ultraviolet-visible absorbance of the *Shewanella* mutant extracts and a commercially available PPIX standard (Sigma Aldrich, St. Louis, Mo.; dissolved in an acetone:$NH_3OH$ (0.1 N) mixture) was measured with a spectrometer (Biowave II, WPA, Biochrom US, Holliston, Mass.) and quartz cuvettes.

System Description: HPLC system: Michrom Bioresources Paradigm MSRB capillary HPLC; Column: Magic MS C18, 5μ, 100 A, 0.5×150 mm. Solvent A: 0.09% Formic Acid, 0.01% TFA, 2% $CH_3CN$, 97.9% water. Solvent B: 0.09% Formic Acid, 0.0085% TFA, 95% $CH_3CN$, 4.9% water. Gradient: 30% to 100% B in 15 minutes, hold 3 minutes, 100% to 30% in 2 minutes. Prep: 1.3 mg of standard was dissolved in 1.3 ml of 100% Methanol, diluted 10 times with 0.1% formic acid, 50% Acetonitrile, 50% Water, load 10 μl on HPLC-UV-MS. 200 μl of sample was dried with Speed-Vac, and then reconstituted with 200 μl of 0.1% formic acid, 50% Acetonitrile, 50% Water, load 10 μl on HPLC-UV-MS. Load: 10 μL on a 40-μL loop; Flow rate: 20 μL/min; UV wavelength: 216 nm. Mass spectrometry system: Bruker Daltonics HCT Ultra Ion trap. Mode: Positive (Target Mass: 500 m/z). Medium: Regular medium used for culture *S. loihica* PV-4 include Luria Broth or other rich nutrient medium. With Marine medium, the PPIX yield at least doubled. Commercialized Marine Broth 2216 medium (e.g., Difco) can also be used. The bacterial mutants of the presently disclosed inventive concepts require no supplementary PPIX.

As shown in FIG. 1, the spectrograms of the commercially-available PPIX standard and the bacterial product constructed in accordance with the presently disclosed inventive concepts were very similar, and the maximum absorbance of both standard and bacterial extract occurred at 405 nm. These results demonstrated that the bacterial product is PPIX or a PPIX-related compound (e.g., heme).

As noted above, PPIX production in an *E. coli* hemH mutant was at the $10^{-9}$M level (Miyamoto et al. 1992). Yang et al. (1996) reported a porphyrin yield of an *E. coli* hemH mutant was 224.6 nmol per gram cell dry weight. Galbis-Martínez et al. (2012) observed production of PPIX at 2.9 μmol/gm dry weight in a hemH mutant of *Myxococcus xanthus*. In the novel mutants presently described, even using a conservative estimation of a PPIX yield of 50 mg/L after overnight culture, the yield of the presently disclosed novel bacterial mutants is about 10,000 times higher than the yield of Miyamoto et al. (1992), at least 1,000 times higher than the yield of Yang et al. (1996), and about 18 times higher than the yield of Galbis-Martínez et al. (2012). In the *Myxococcus xanthus* study of Galbis-Martínez et al., the medium had to be supplemented with hemin (a source of PPIX) for the mutant strain to survive. The bacterial mutants of the presently disclosed inventive concepts require no such supplementation. Moreover, while hemin is relatively cheap ($30-40 per gram) compared to PPIX, it is impossible to use it in the large quantities necessary for industrial level production of PPIX using the *Myxococcus xanthus* mutant strain.

Figure 2:
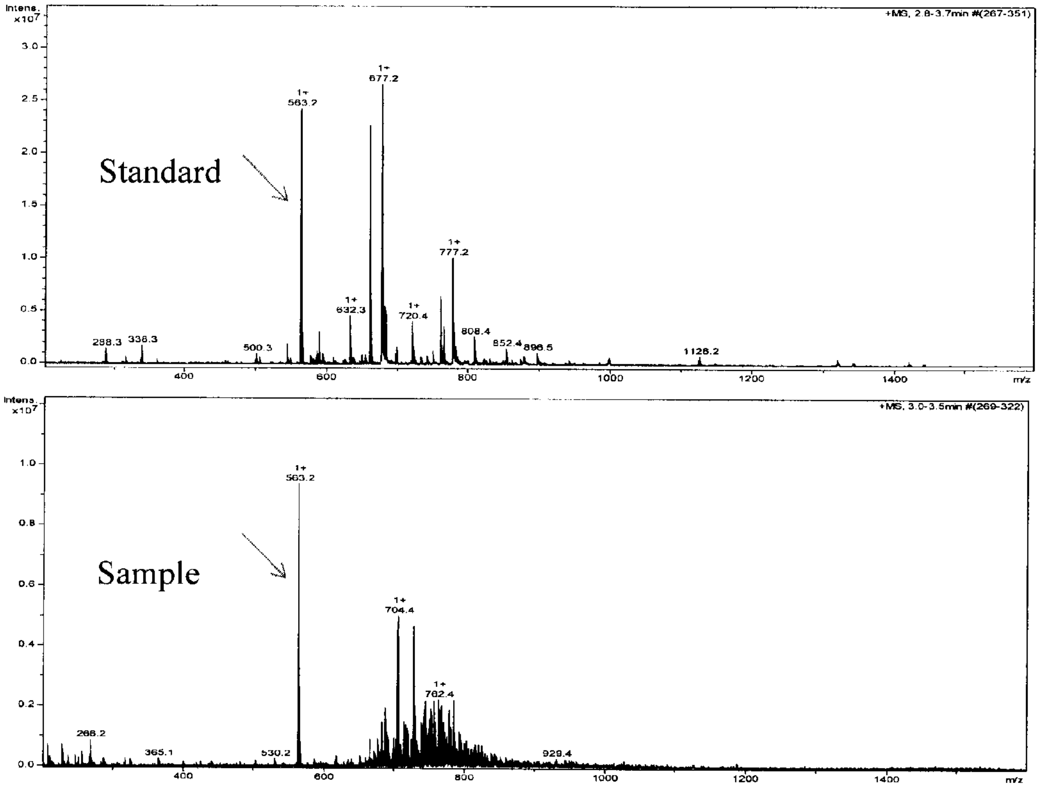
FIG. 2. Mass spectra of commercially-available PPIX standard (upper panel) and the bacterial product sample produced in accordance with the presently disclosed inventive concepts (lower panel); these spectra demonstrate that the bacterial product ("sample") is more pure. Peaks indicated by arrows represent PPIX. Units of the x-axis are mass to charge (M/Z) in Kg/C.

The further structural analyses were conducted at the University of Oklahoma Health Sciences Center (including mass spectroscopy (MS) and high-performance liquid chromatography (HPLC)) and Oak Ridge National Laboratory (Fourier transform infrared spectroscopy (FTIR) and fluorescence analysis). The PPIX of the bacterial product had essentially the same mass (molecular weight MW) as the commercial standard PPIX (FIG. 2). The commercial PPIX standard showed two major peaks (563.2 and 677.2), whereas the bacterial PPIX product showed just a single major peak at 563.2, indicating that (i) the commercial standard PPIX either contains a chiral molecule in which the optical isomer resulted in the splitting, or (ii) the commercial standard PPIX is not pure (FIG. 2). Therefore, at least one embodiment the biotechnological process of the presently disclosed inventive concepts produces a PPIX having greater purity than the commercial process, which uses livestock blood as a source of PPIX.

Figure 3:
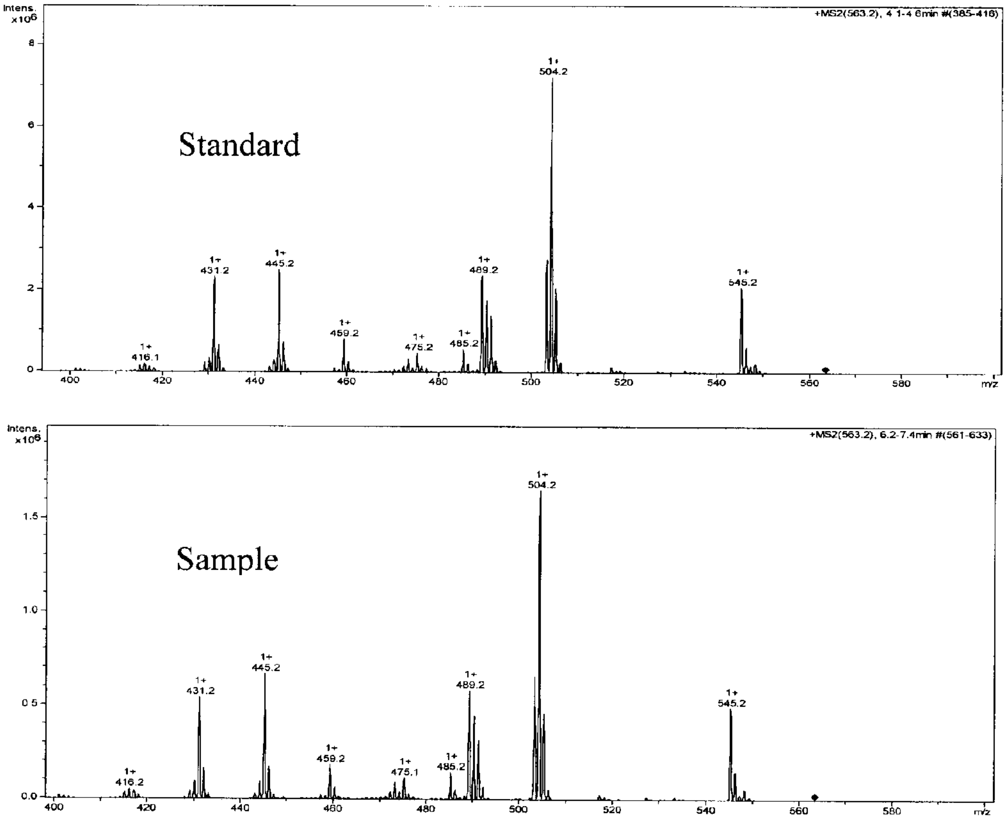
FIG. 3. ESI (Electrospray Ionization)-MS/MS (precursor ion: 563.2-PPIX) showing the identical structure of PPIX in the commercially-available standard (upper panel) and the bacterial product produced in accordance with the presently disclosed inventive concepts (lower panel). Units of the x-axis are mass to charge (M/Z) in Kg/C.
Figure 4:
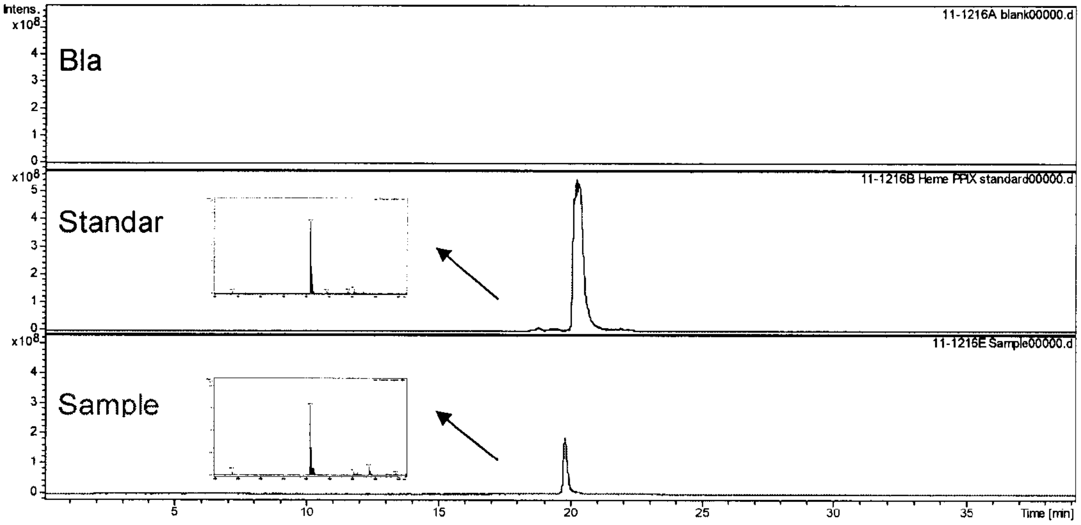
FIG. 4. Comparison of HPLC-MS extract ion chromatograms EIC563.2±0.3 (Blank, Standard, Sample (bacterial product)).
Figure 5:
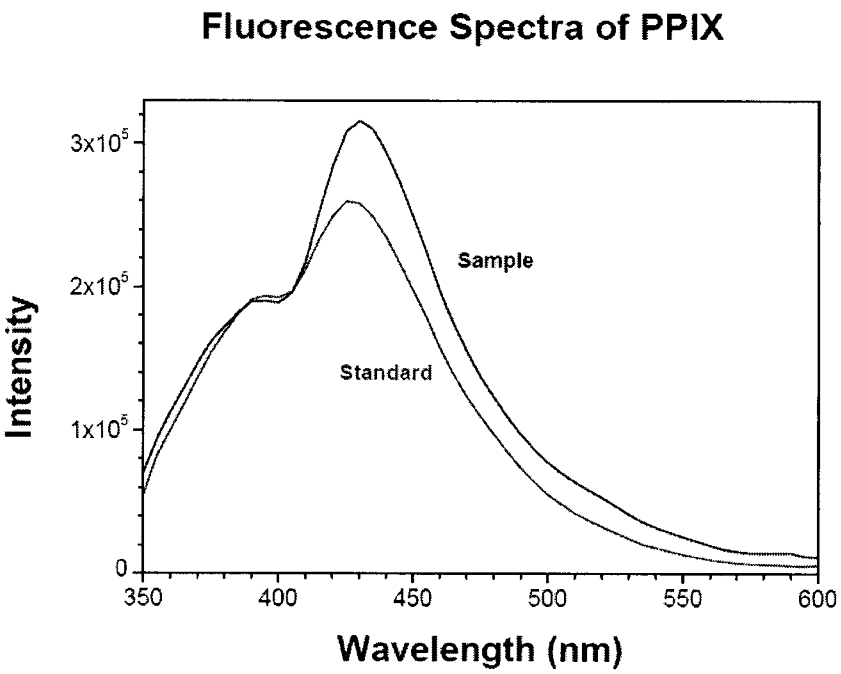
FIG. 5. Fluorescence spectra of the commercially-available PPIX standard and PPIX of the bacterial product produced in accordance with the presently disclosed inventive concepts, demonstrating their similarity.
Figure 6:
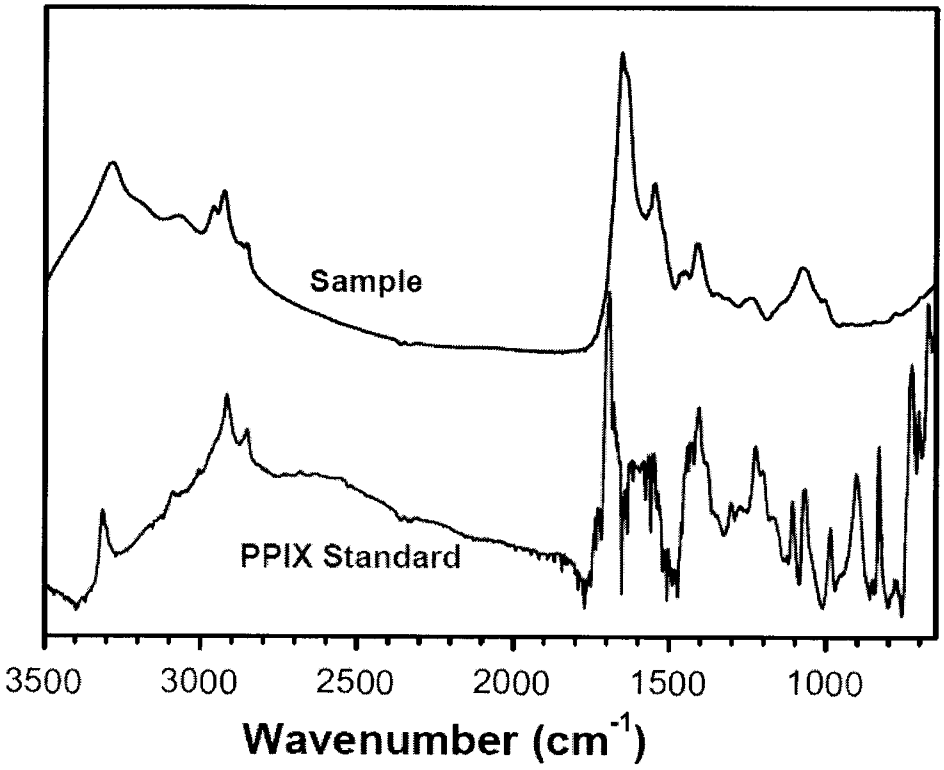
FIG. 6. Fourier Transform Infrared (FTIR) Spectroscopy of the commercially-available PPIX standard and PPIX of the bacterial product produced in accordance with the presently disclosed inventive concepts.

The fragment profile of the bacterial product is also the same as that of the 563.2 peak (MW 563 g/Mole) of the commercial PPIX standard (FIG. 3). Both the commercial PPIX standard and the bacterial product are washed out at almost the same time on HPLC (FIG. 4). FIG. 5 shows the similarity in fluorescence spectra of the commercially-available PPIX standard and PPIX of the bacterial product produced by the presently disclosed mutants. FIG. 6 shows a Fourier Transform Infrared (FTIR) spectrograms of the commercially-available PPIX standard and PPIX of the bacterial product, again indicating the similarity of the chemical profile.

Example 2

In at least one embodiment, the presently disclosed inventive concepts include mutants of *Shewanella* species, including but not limited to *S. loihica* PV-4 (or other *Shewanella* strains), comprising a mutation in the DNA sequence of the shew_2229 (hemH1) gene (SEQ ID NO:1). SEQ ID NO:1 is the complete open reading frame of shew_2229. The mutant may further comprise an expression sequence useful in the expression (e.g., a promoter sequence) of the mutant, including, but not limited to SEQ ID NO:3, SEQ ID NO:4, SEQ ID NO:5 and/or SEQ ID NO:6. The expression sequence may be upstream or downstream of SEQ ID NO:1. In at least one embodiment, the presently disclosed inventive concepts include the use of said mutants for producing PPIX. As noted above, the mutation of the shew_2229 gene may be any effective means by which the function of the gene can be disrupted, including but not limited to insertions, deletions, substitutions, and/or inversions.

In at least one embodiment, the shew_2229 mutant comprises a transposon within the ORF, such as but not limited to, a transposon comprising an R6K replicon and a kanamycin resistance gene ($Km^r$); the transposon may optionally be flanked by two inverse repeat sequences. The deletion mutants comprise at least one deletion of at least one or more nucleotide positions in the ORF, wherein the deletion(s) causes disruption of normal expression of the gene. The insertion mutants comprise at least one insertion of at least one or more additional nucleotides at a position in the ORF, wherein the insertion(s) causes disruption of normal expression of the gene. The non-limiting example of an inserted transposon is an example of such an insertion. The substitution mutants comprise at least one substitution in at least one or more nucleotide positions in the ORF, wherein the insertion(s) causes disruption of normal expression of the gene. The inversion mutants comprise inversions in the order of at least two or more nucleotide positions in the ORF, wherein the inversions cause disruption of normal expression of the gene. In other embodiments, the mutants may comprise more that one type of mutation, for example an insertion and a deletion, an insertion and a substitution, a deletion and an inversion, or any combination of two or more of an insertion, deletion, substitution, and inversion.

As indicated, the mutation in the shew_2229 gene may comprise one or more substitutions, insertions, deletions, and/or inversions, as long as they cause disruption or diminishment of the expression of the gene. The substitution, insertion, deletion, or inversion may comprise one or more bases of SEQ ID NO:1 numbering 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, or 31-40, or 41-50, or 51-60, or 61-70, or 71-80, or 81-90, or 91-100, or 101-200, or 201-300, or 301-400, or 401-500, or 501-600, or 601-700, or 701-800, or 801-900, or 901-1000, or more bases, up to and including the entire sequence SEQ ID NO:1, and all integers inclusive in the ranges listed above, such as but not limited to 54, 98, 345, 666, and 833, including all ranges between any of such integers, such as but not limited to 1-25, 41-450, and 5-100.

Example 3

In one embodiment, the presently disclosed inventive concepts include mutants of *Shewanella* species, including but not limited to *S. loihica* PV-4 (or other *Shewanella* strains), comprising a mutation in the DNA sequence of the shew_1140 (hemH2) gene (SEQ ID NO:2). SEQ ID NO:2 is the complete open reading frame of shew_1140. The mutant may further comprise an expression sequence useful in the expression (e.g., a promoter sequence) of the mutant, including but not limited to, SEQ ID NO:3, SEQ ID NO:4, SEQ ID NO:5 and/or SEQ ID NO:6. The expression sequence may be upstream or downstream of SEQ ID NO:2. In at least one embodiment, the presently disclosed inventive concepts include the use of said mutants for producing PPIX. As noted above, the mutation of the shew_1140 gene may be any effective means by which the function of the gene can be disrupted, including but not limited to, insertion(s), deletion(s), substitution(s), and/or inversion(s). In at least one embodiment, the shew_1140 mutant comprises a transposon within the ORF, such as but not limited to, a transposon comprising an R6K replicon and a kanamycin resistance gene ($Km^r$); the transposon may optionally be flanked by two inverse repeat sequences. The deletion mutants comprise deletions of at least one or more nucleotide positions in the ORF which causes disruption of normal expression of the gene. The insertion mutants comprise insertions of at least one or more additional nucleotides at a position in the ORF which causes disruption of normal expression of the gene. The non-limiting example of an inserted transposon is an example of such an insertion. The substitution mutants comprise substitution(s) in at least one or more nucleotide positions in the ORF, wherein the substitution(s) causes disruption of normal expression of the gene. The inversion mutants comprise inversion(s) in the order of at least two or more nucleotide positions in the ORF, wherein the inversion(s) causes disruption of normal expression of the gene. In other embodiments the mutants may comprise more that one type of mutation, for example, an insertion and a deletion, an insertion and a substitution, a deletion and an inversion, or any combination of two or more of an insertion, deletion, substitution, and inversion. As indicated, the mutation in the shew_1140 gene may comprise one or more substitution(s), insertion(s), deletion(s), and/or inversion(s), as long as they cause disruption or diminishment of the normal expression of the gene. The substitution(s), insertion(s), deletion(s), and/or inversion(s) may comprise one or more bases of SEQ ID NO:2 numbering 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, or 31-40, or 41-50, or 51-60, or 61-70, or 71-80, or 81-90, or 91-100, or 101-200, or 201-300, or 301-400, or 401-500, or 501-600, or 601-700, or 701-800, or 801-900, or 901-1000, or more bases, up to and including the entire sequence SEQ ID NO:2, and all integers inclusive in the ranges listed above, such as but not limited to, 54, 98, 345, 666, and 833, including all ranges between any of such integers, such as but not limited to, 1-25, 41-450, and 5-100.

Example 4

In an alternate embodiment, the presently disclosed inventive concepts include mutants of *S. loihica* PV-4 (or other *Shewanella* strains) which comprise mutations in both of the shew__2229 and shew__1140 genes (SEQ ID N01: and SEQ ID NO:2). The mutations may comprise any of those described in Examples 2 and 3.

Example 5

In an alternate embodiment, the presently disclosed inventive concepts include use of RNA polynucleotides which are able to specifically disrupt by RNA interference the transcription and/or translation of mRNA molecules in *Shewanella* species comprising wild-type shew__2229 and/or shew__1140, thereby inhibiting production of the ferrochelatase protein encoded by either of shew__2229 and/or shew__1140. Examples of such interfering RNA molecules include, but are not limited to, SEQ ID NOS:7-16, and larger RNA molecules comprising these sequences, and double-stranded RNA molecules comprising these sequences and their complementary sequences.

The presently disclosed inventive concepts are directed in certain embodiments to a method of producing protoporphyrin IX by (1) cultivating a strain of *Shewanella* bacteria in a culture medium under conditions suitable for growth thereof, the strain of *Shewanella* bacteria comprising at least one mutant hemH gene which is incapable of normal expression, thereby causing an accumulation of protoporphyrin IX, and (2) recovering the protoporphyrin IX from the culture medium. In certain embodiments of the method, the strain of *Shewanella* bacteria is a strain of *S. loihica*. In certain embodiments of the method, the strain of *Shewanella* bacteria is *S. loihica* PV-4. In certain embodiments, the mutant hemH gene of the strain of *Shewanella* bacteria may be a mutant of shew__2229, or of shew__1140, or of both shew__2229 and shew__1140. In certain embodiments, the protoporphyrin IX produced in the culture medium of the method may be recoverable in an amount of at least about 0.1 mg per ml of culture medium. In certain embodiments of the method, the addition of supplementary protoporphyrin IX to the culture medium is not necessary for the accumulation of protoporphyrin IX during the cultivation of the strain of *Shewanella* bacteria. In certain embodiments of the method, the strain of *Shewanella* bacteria may have been transformed with the at least one mutant hemH gene. In other embodiments, the presently disclosed inventive concepts are directed to mutant strains of *Shewanella* bacteria having at least one mutant hemH gene which is incapable of normal expression, thereby causing an accumulation of protoporphyrin IX during cultivation of the bacteria. In certain embodiments, the strain of *Shewanella* bacteria is a strain of *S. loihica*, and more specifically may be *S. loihica* PV-4. In certain embodiments, the mutant hemH gene of the strain of *Shewanella* bacteria may be a mutant of shew__2229 and/or of shew__1140.

While the presently disclosed inventive concepts are described herein in connection with certain embodiments so that aspects thereof may be more fully understood and appreciated, it is not intended that the presently disclosed inventive concepts be limited to these particular embodiments. On the contrary, it is intended that all alternatives, modifications, and equivalents are included within the scope of the presently disclosed inventive concepts as defined herein. Thus the examples described above, which include particular embodiments, will serve to illustrate the practice of the presently disclosed inventive concepts, it being understood that the particulars shown are by way of example only and are for purposes of illustrative discussion of particular embodiments of the presently disclosed inventive concepts only and are presented in the cause of providing what is believed to be the most useful and readily understood description of procedures as well as of the principles and conceptual aspects of the presently disclosed inventive concepts. Changes may be made in the formulation of the various compositions described herein, or in the steps or the sequence of steps of the methods described herein, without departing from the spirit and scope of the presently disclosed inventive concepts.

What is claimed is:

1. A method of producing protoporphyrin IX, comprising:

cultivating a strain of *Shewanella* bacteria in a culture medium under conditions suitable for growth thereof, the strain of *Shewanella* bacteria comprising at least one mutant hemH gene which is incapable of normal expression, thereby causing an accumulation of protoporphyrin IX; and recovering the protoporphyrin IX from the culture medium.

2. The method of claim 1, wherein the strain of *Shewanella* bacteria is a strain of *S. loihica.*

3. The method of claim 1, wherein the strain of *Shewanella* bacteria is *S. loihica* PV-4.

4. The method of claim 1, wherein the mutant hemH gene is a mutant of shew__2229 and/or a mutant of shew__1140.

5. The method of claim 1, wherein the protoporphyrin IX produced in the culture medium is recoverable in an amount of at least about 0.1 mg per ml of culture medium.

6. The method of claim 1, wherein the addition of supplementary protoporphyrin IX to the culture medium is not necessary for the accumulation of protoporphyrin IX during the cultivation of the strain of *Shewanella* bacteria.

7. The method of claim 1, wherein said strain of *Shewanella* bacteria is transformed with said at least one mutant hemH gene.

8. A mutant strain of *Shewanella* bacteria comprising at least one mutant hemH gene which is incapable of normal expression, thereby causing an accumulation of protoporphyrin IX during cultivation of the mutant strain of *Shewanella* bacteria in a culture medium.

9. The mutant strain of *Shewanella* bacteria of claim 8, comprising a strain of *S. loihica.*

10. The mutant strain of *Shewanella* bacteria of claim 8, comprising *S. loihica* PV-4.

11. The mutant strain of *Shewanella* bacteria of claim 8, wherein the mutant hemH gene is a mutant of at least one of shew__2229 and shew__1140.

* * * * *

UNITED STATES PATENT AND TRADEMARK OFFICE

CERTIFICATE OF CORRECTION

PATENT NO. : 9,273,334 B2
APPLICATION NO. : 14/349171
DATED : March 1, 2016
INVENTOR(S) : Jizhong Zhou et al.

It is certified that error appears in the above-identified patent and that said Letters Patent is hereby corrected as shown below:

In the Specification:
Column 8, line 2: Delete "OD" and replace with -- (JGI) --
Column 13, line 9: Delete "N01:" and replace with -- NO:1 --

Signed and Sealed this
Third Day of May, 2016

Michelle K. Lee
*Director of the United States Patent and Trademark Office*

SEQUENCE LISTING

```
<160> NUMBER OF SEQ ID NOS: 16

<210> SEQ ID NO 1
<211> LENGTH: 1014
<212> TYPE: DNA
<213> ORGANISM: Shewanella loihica PV-4

<400> SEQUENCE: 1

ttgaataaag tcgacaactt atctcccgct aagcttggtg tcttgctggt taatctcggc      60

acacccgata caccaacgcc taaagatgta aagcagttct taaaacagtt tctcagcgac     120

ccgcgcgtgg tcgatctaaa tccctggatc tggaaaccca tactcaatgg catcatatta     180

aatacgcgcc ccaaggccgt agccaagctc tatgagtcta tctggtggcc cgagggctcg     240

cctctgatgg tgatcagtga gcgccaacgt gaagcgctga gtgcgattct aaaagcgcgt     300

catggtagcg atattccggt ggagttgggg atgagttatg gcaatccctc actgtcgtcg     360

gggatagaca agctggtggc tcagggtgtt gagcgcctgg tggtgctgcc gctatatcct     420

cagtattcct gctccaccgt ggcaccggta ttcgatgcca tcgccagtga ctataagggc     480

agacgcaact atcctgagac ccgcttcagt aaagagtatt tcgagcaccc ggcctatatc     540
```

-continued

```
gcggcgctgg caggttctgt gcggcgtcat tggcaagata agggccaggg cgattgcctc    600

ttgatgtcct ttcatggcgt gcccctgcgt tatgtgaccg agggtgaccc ctatcagcgt    660

cagtgtcaac gtactgccga gctgctggcc gcggccttgg ggcttacaga gtctcagtgg    720

cgcctgtgtt ttcaatcgaa atttggtaag gaggagtggc tgacgccggc aacggatgcg    780

ctgctcgaga gtttgccggg taagggggtt aagcgcgtgg atattctctg tccggccttt    840

gccgtggatt gtttggagac gcttgaagag atctccattg gcggcaagga gagctttatc    900

gaggccggcg gtgaggacta tcatttcatc ccttgtttga acgaggatga agcgcatatg    960

cagctgctcg cggacttggt cgatcaacag gcggcgggct ggcttaaatc ttaa         1014
```

```
<210> SEQ ID NO 2
<211> LENGTH: 1068
<212> TYPE: DNA
<213> ORGANISM: Shewanella loihica PV-4

<400> SEQUENCE: 2

gtgcaaagaa aaagaaagcg cgttgggcaa cacagacaaa aacaaggaat cactttggca     60

aaatactttg gattgaataa acagcagggc catggcggtc gtggcaagac gacggtactg    120

ctgatgaatc tgggcacacc ggatgcgcca actacgggcg ccgtgcgtcg ttatctggcg    180

gagtttctct cggatccccg cgtggtggag atccctaagc tggtgtggat gctgatactg    240

cacggcatca ttttacgcat ccgcccggca aagtctgccg ccctgtatca gtctatctgg    300

acggagcagg gctcgcctct gatggcgatc acccaggcgc agcgggacaa gctcgcgcaa    360

aagctgagtg aaaatggcag tgacgttaat gtggatttct gcatgcgtta cggcgagccg    420

agcgttaagg agacgctgag acgtctccat agcgagggaa ccgacaagct catcgtcttg    480

cccctctatc ctcagtacgc cgcgcccacc acggcctcgg ccttcgacgc cctgaccaag    540

gagctgattt cgtggcgcta cctgccgtcg ctgcacttta tcaacagcta tcatgaccac    600

ccagattata ttgcggcgct ggctgactct atcgctaagg acttcgagca acatggcaag    660

ccgaagaagt tagtgctctc ttaccatggc atgcccgagc gcaacctgaa tctcggcgac    720

ccctactact gcctgtgtca gaagaccacc cgcctggtgg tggaacgcct agggctcact    780

gatgacgact atatcaccac cttccagtcg cgctttggca aggccaagtg gctcggcccc    840

tacacggatg ccagcctgga ggcgttagcg aaagagggcg tggatgatgt ggccatcgtc    900

tgcccggcgt tcagcgccga ctgtctggag acactcgagg agatcgagca tgagaaccgg    960

gatgtgttca cccaggccgg tggcagcgag tatcgttata ttccctgtct caatgaccag   1020

gaactgcata ttcagatgat ggtgaatctg gtgaggccgt atctttaa                1068
```

```
<210> SEQ ID NO 3
<211> LENGTH: 136
<212> TYPE: DNA
<213> ORGANISM: Shewanella loihica PV-4

<400> SEQUENCE: 3

ttccgctgct ataaagtgaa gcgctatatg agctgcttct catatttgaa aaagcccacc     60

taggtgggct ttttttatgc aagggtgggt gctagcctag cgctatcctt gccagagaat    120

atgagtagag taattc                                                    136
```

```
<210> SEQ ID NO 4
<211> LENGTH: 100
<212> TYPE: DNA
```

-continued

<213> ORGANISM: Shewanella loihica PV-4

<400> SEQUENCE: 4

```
gcaaagaatc ttaggtaaac ggcataaatc actgcccgat gctattttat atggtacgat     60

ctgccgccgt ttttttgagg cgatggcgtc cgcgtggcat                           100
```

<210> SEQ ID NO 5
<211> LENGTH: 125
<212> TYPE: DNA
<213> ORGANISM: Shewanella loihica PV-4

<400> SEQUENCE: 5

```
ctcttattgc actttgaaaa aaccgataat ccctttatcg gttttttat gtgtggcgat      60

tgatctctaa ggggccgaac cgcgtactga tgcccatgca tcattagcct cggccaggtg    120

cccag                                                                 125
```

<210> SEQ ID NO 6
<211> LENGTH: 100
<212> TYPE: DNA
<213> ORGANISM: Shewanella loihica PV-4

<400> SEQUENCE: 6

```
cttggttagg ttaaaggggg gattcttggt tgcctcaagg ggggcattag tttgcttgat     60

tagcatttgg cgacatgctc acttattaaa tgagttgaag                           100
```

<210> SEQ ID NO 7
<211> LENGTH: 52
<212> TYPE: RNA
<213> ORGANISM: Artificial Sequence
<220> FEATURE:
<223> OTHER INFORMATION: iRNA for SEQ ID NO:1 and/or 2

<400> SEQUENCE: 7

```
caagcuggug gcucagggug uugagcucaa cacccugagc caccagcuug uc             52
```

<210> SEQ ID NO 8
<211> LENGTH: 52
<212> TYPE: RNA
<213> ORGANISM: Artificial Sequence
<220> FEATURE:
<223> OTHER INFORMATION: iRNA for SEQ ID NO:1 and/or 2

<400> SEQUENCE: 8

```
gagaauauga guagaguaau ucuugcaaga auuacucuac ucauauucuc ug             52
```

<210> SEQ ID NO 9
<211> LENGTH: 52
<212> TYPE: RNA
<213> ORGANISM: Artificial Sequence
<220> FEATURE:
<223> OTHER INFORMATION: iRNA for SEQ ID NO:1 and/or 2

<400> SEQUENCE: 9

```
auaugagcug cuucucauau uugaauucuu uuaugagaag cagcucauau ag             52
```

<210> SEQ ID NO 10
<211> LENGTH: 52
<212> TYPE: RNA
<213> ORGANISM: Artificial Sequence
<220> FEATURE:
<223> OTHER INFORMATION: iRNA for SEQ ID NO:1 and/or 2

<400> SEQUENCE: 10

-continued

```
ucaguaaaga guauuucgag cacccgggug cucgaaauac uauuuacuga ag              52


<210> SEQ ID NO 11
<211> LENGTH: 52
<212> TYPE: RNA
<213> ORGANISM: Artificial Sequence
<220> FEATURE:
<223> OTHER INFORMATION: iRNA for SEQ ID NO:1 and/or 2

<400> SEQUENCE: 11

ccaggaucug gaaacccaua cucaauugag uaugggguuuc cagauccagg ga             52


<210> SEQ ID NO 12
<211> LENGTH: 52
<212> TYPE: RNA
<213> ORGANISM: Artificial Sequence
<220> FEATURE:
<223> OTHER INFORMATION: iRNA for SEQ ID NO:1 and/or 2

<400> SEQUENCE: 12

agccaagcuc uaugagucua ucuggccaga uagacucaua gagcuuggcu ac              52


<210> SEQ ID NO 13
<211> LENGTH: 52
<212> TYPE: RNA
<213> ORGANISM: Artificial Sequence
<220> FEATURE:
<223> OTHER INFORMATION: iRNA for SEQ ID NO:1 and/or 2

<400> SEQUENCE: 13

cuaucauuuc aucccuuguu ugaacguuca aacaagggau gaaaugauag uc              52


<210> SEQ ID NO 14
<211> LENGTH: 52
<212> TYPE: RNA
<213> ORGANISM: Artificial Sequence
<220> FEATURE:
<223> OTHER INFORMATION: iRNA for SEQ ID NO:1 and/or 2

<400> SEQUENCE: 14

cuaucagcgu cagugucaac guacuaguac guugacacug acgcugauag gg              52


<210> SEQ ID NO 15
<211> LENGTH: 52
<212> TYPE: RNA
<213> ORGANISM: Artificial Sequence
<220> FEATURE:
<223> OTHER INFORMATION: iRNA for SEQ ID NO:1 and/or 2

<400> SEQUENCE: 15

ggauuguuug gagacgcuug aagagcucuu caagcgucuc caaacaaucc ac              52


<210> SEQ ID NO 16
<211> LENGTH: 52
<212> TYPE: RNA
<213> ORGANISM: Artificial Sequence
<220> FEATURE:
<223> OTHER INFORMATION: iRNA for SEQ ID NO:1 and/or 2

<400> SEQUENCE: 16

ccucaguauu ccugcuccac cguggccacg guggagcagg aauacugagg au              52
```